US00PP35631P2

(12) United States Plant Patent
Baugher

(10) Patent No.: US PP35,631 P2
(45) Date of Patent: Feb. 6, 2024

(54) APPLE TREE NAMED 'JHB 619 CLTV'

(50) Latin Name: ***Malus* x *domestica***
Varietal Denomination: JHB 619 Cltv

(71) Applicant: Adams County Nursery, Inc., Aspers, PA (US)

(72) Inventor: John H. Baugher, Aspers, PA (US)

(73) Assignee: Adams County Nursery, Inc., Aspers, PA (US)

( * ) Notice: Subject to any disclaimer, the term of this patent is extended or adjusted under 35 U.S.C. 154(b) by 0 days.

(21) Appl. No.: 17/979,188

(22) Filed: Nov. 2, 2022

(51) Int. Cl.
*A01H 5/08* (2018.01)
*A01H 6/74* (2018.01)

(52) U.S. Cl.
USPC ..... Plt./163

(58) Field of Classification Search
USPC ..... Plt./163
CPC ..... A01H 5/08; A01H 5/00; A01H 6/747418
See application file for complete search history.

(56) References Cited

U.S. PATENT DOCUMENTS

PP7,590 P * 7/1991 Lichtenauer ..... Plt./163
PP8,049 P * 12/1992 Swillen ..... Plt./163

* cited by examiner

*Primary Examiner* — June Hwu
(74) *Attorney, Agent, or Firm* — Patrick J. Daugherty; Daugherty & Del Zoppo Co., LPA

(57) ABSTRACT

A new and distinct apple variety named 'JHB 619 Cltv' is provided. This variety is distinguished from other apple varieties by the unique color of its fruit.

5 Drawing Sheets

Latin name of genus and species: *Malus* x *domestica*.
Variety denomination: 'JHB 619 Cltv'.

BACKGROUND OF THE INVENTION

The present invention relates to a new and distinct variety of apple tree named 'JHB 619 Cltv' that resulted from a limb mutation on a 'Jonagold De Coster' tree (U.S. Plant Pat. No. 8,049). The resulting tree was selected when growing in a cultivated area in an orchard managed by Adams County Nursery in Menhallen Township, Pennsylvania in a block named "Bull Valley."

Figure 1:
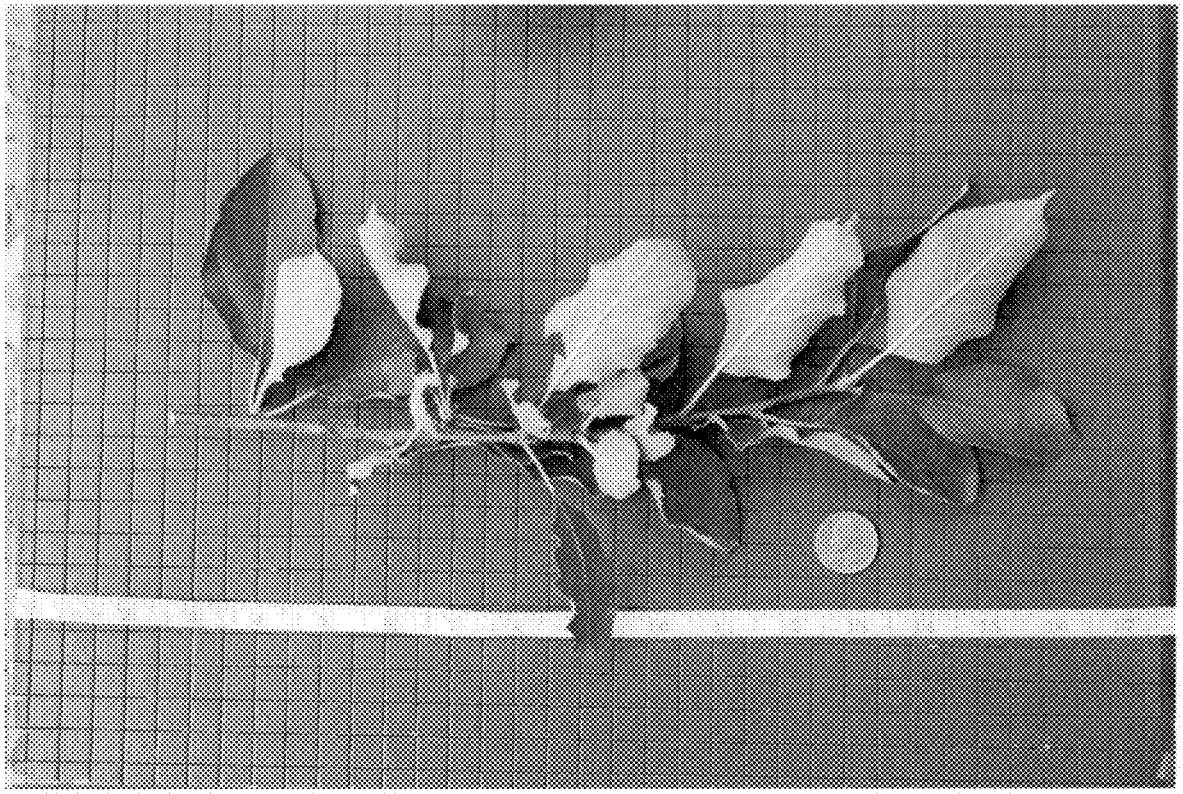
FIG. 1 is a color photograph taken on Oct. 2, 2015, of a characteristic twig of a 'JHB 619 Cltv' tree at four years of age bearing typical leaves of the foliage.
Figure 2:
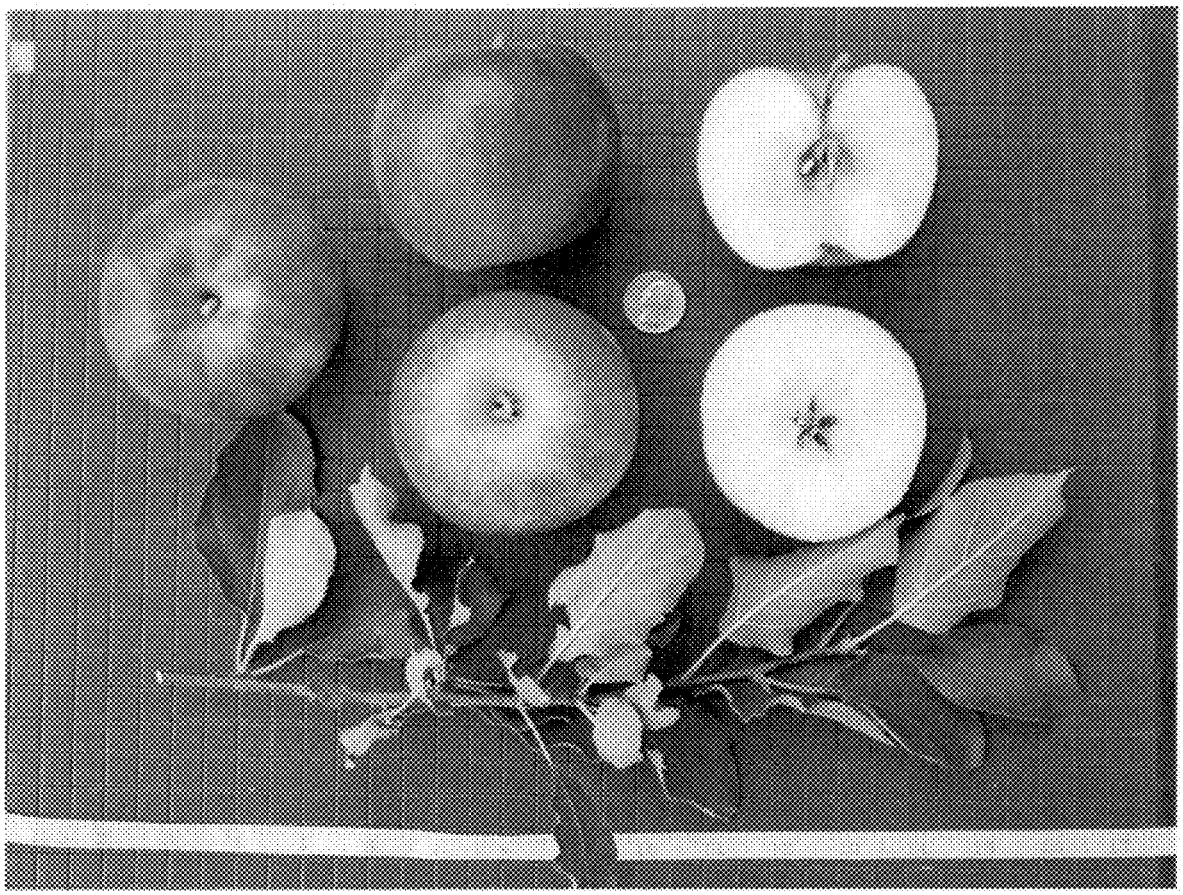
FIG. 2 is a color photograph taken on Oct. 6, 2015, of characteristic mature fruit and a characteristic twig bearing typical leaves of the foliage of a 'JHB 619 Cltv' tree at four years of age. Whole fruit are presented in three positions and both a transverse and longitudinal cross section to illustrate their globose shape, flaring cavity and persistent sepals with erect tips.
Figure 3:
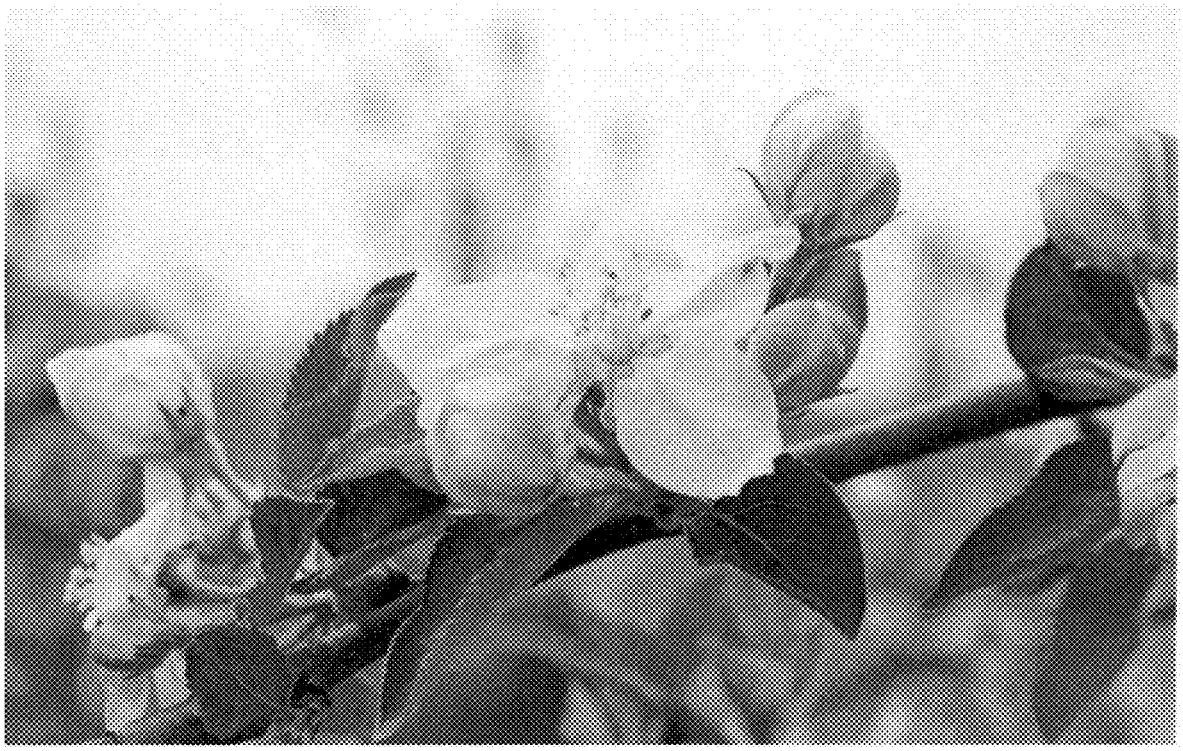
FIG. 3 is a color photograph of a characteristic twig that illustrates the typical open flowers and flower buds of 'JHB 619 Cltv' observed on a tree at four and one-half years of age in a managed orchard in Aspers, Pennsylvania on Apr. 19, 2016.
Figure 4:
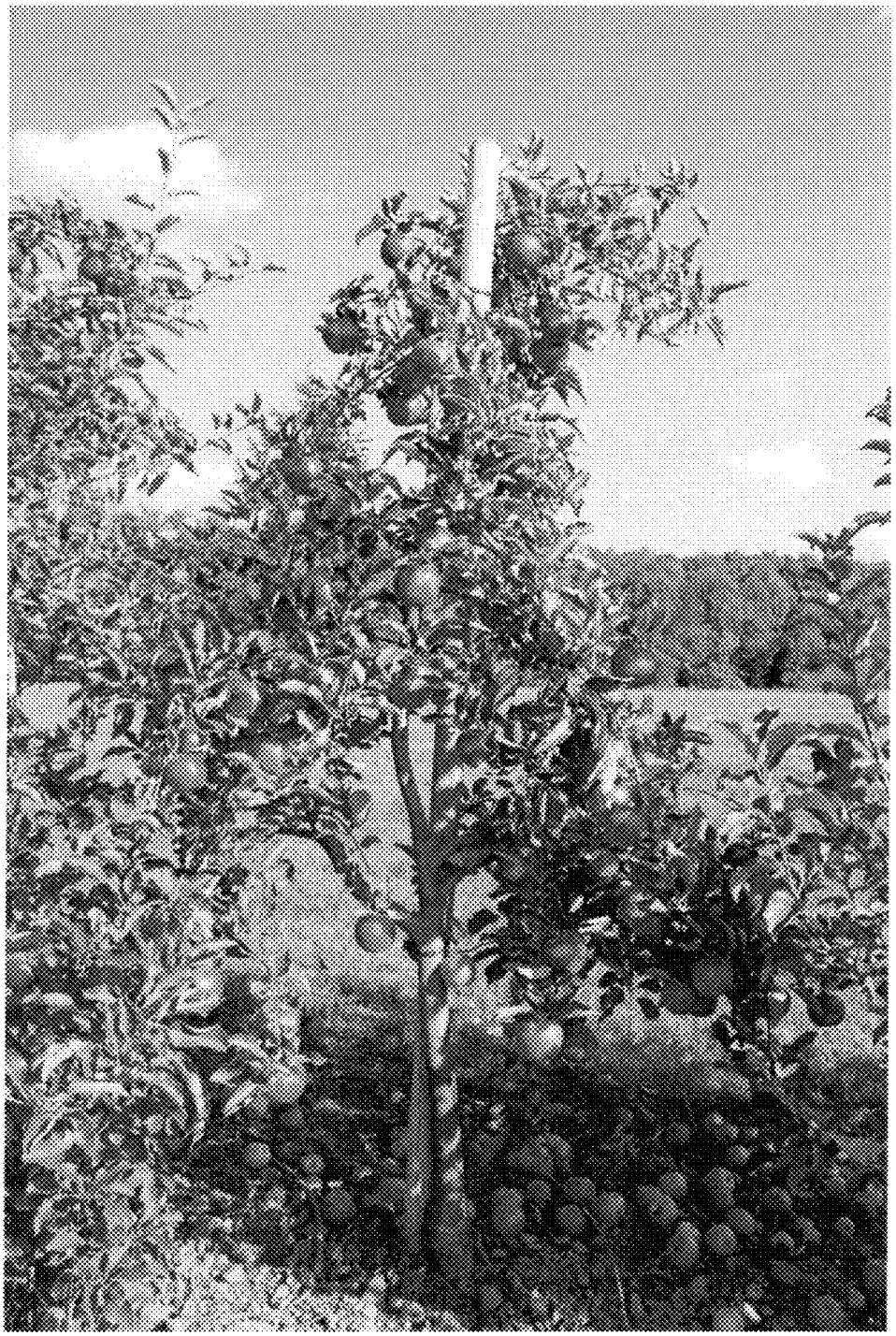
FIG. 4 is a color photograph of a tree of 'JHB 619 Cltv', at time of harvest that illustrates the upright growth habit of a tree at four years of age in a managed orchard on Oct. 19, 2015.
Figure 5:
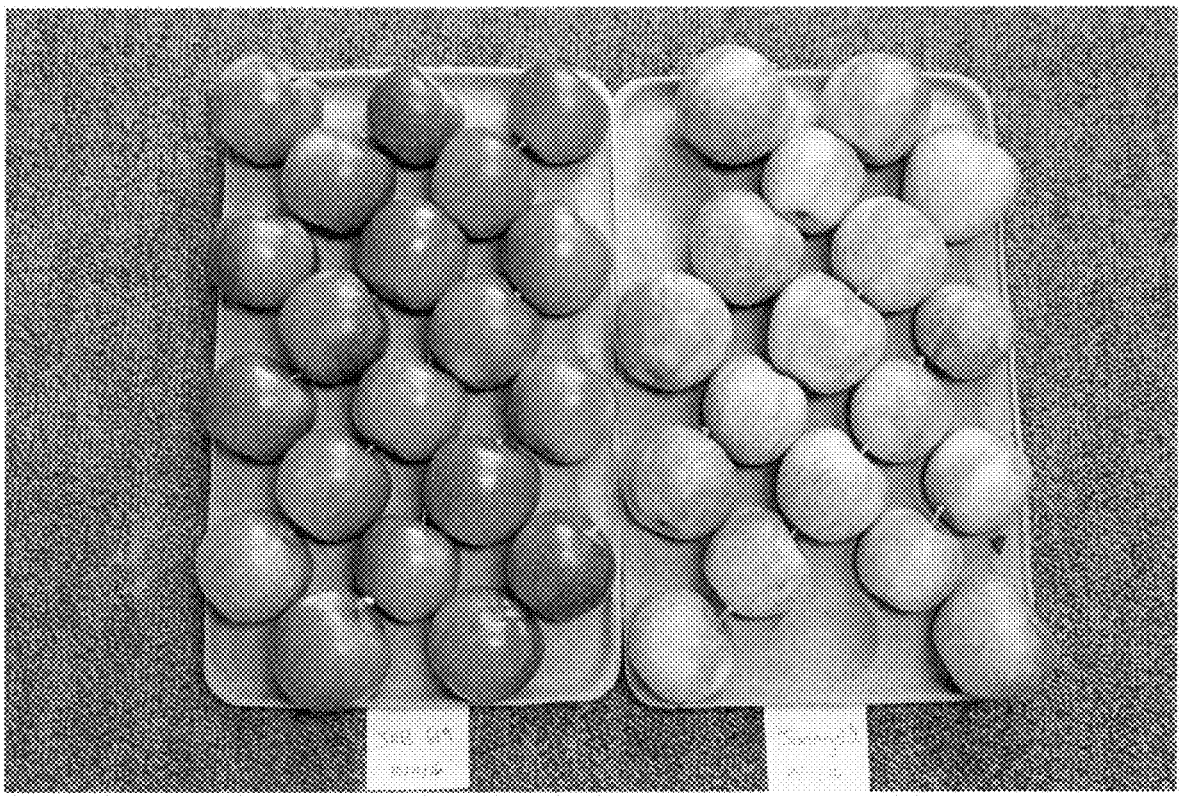
FIG. 5 is a color photograph of the fruit color comparison of apples harvested on the same date. On left, apples of 'JHB 619 Cltv' harvested on Oct. 11, 2016, compared to, on right, a crate of 'Jonagold De Coster' apples harvested on the same date. The photograph shows that apples produced by 'JHB 619 Cltv' have distinctively more color than apples produced by 'Jonagold De Coster'.

The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

The 'JHB 619 Cltv' variety is distinguished from the related known cultivar 'Jored' (U.S. Plant Pat. No. 8,851 P): while both are strains of the unpatented 'Jonagold' variety, 'JHB 619 Cltv' produces fruit with distinctly different overcolor and lenticels color values and no observed chimaera stripes, as discussed more fully below. 'JHB 619 Cltv' also differs from parent 'Jonagold De Coster' in producing fruit that have an average of 55-65% more red overcolor as a blush over the surface, distinctly different ground coloring and stem pit coloring, and more prominent lenticels, as discussed more fully below.

The variety was asexually reproduced in a commercial orchard block in Aspers, PA. Asexual reproduction of this new variety by topworking onto M9(337) rootstock (non-patented) shows that the claimed cultivar is stable and reproduces true to type in successive generations of asexual reproduction.

The following detailed description of the 'JHB 619 Cltv' variety is based on observations of asexually reproduced trees of 4 years of age growing on M9(337) rootstock (non-patented), and measurements taken on Jun. 30, 2023, in a managed orchard in Adams County, Aspers, PA.

Color designations are made with reference to *The Royal Horticultural Society* (*R.H.S.*) *Colour Chart* (1966 Ed.). However, colors are approximate as color depends on horticultural practices, such as light level, fertilization rate, and other conditions. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise.

Scientific name: *Malus* x *domestica*.

Parentage: A limb sport mutation in a planting of 'Jonagold De Coster' trees. Asexually reproduced by top-working and also bud grafting.

Tree: One year old shoot: attitude of leaf in relation to shoot is upward; average internode length is 29.8 mm; average diameter at base of new shoot is 6.25 mm.; pubescent along entire shoot, medium density and easily removed when handling the shoot, and short hairs are Greyed-White (156D) in color.

*Vigor*.—Strong.

*Plant hardiness zones*.—United States Department of Agriculture (USDA) zones 4-8; growth of plants has been observed in zone 6b.

*Dormant flower bud cold tolerance*.—At least to −17 degrees centigrade.

*Overall shape*.—Ramified, upright-spreading.

*Height*.—Moderate as compared to other apple trees on M9(337) rootstock.

*Width*.—Moderate as compared to other apple trees on M9(337) rootstock.

Trunk and branches:

*Trunk bark color*.—Greyed-brown (RHS 201B).

*Primary branches*.—Branches are 19 mm. in diameter, having about 40 to 50-degree crotch angles, and greyed brown (RHS 201B) in color.

*Branch angle*.—Typically about 40 to 50 degrees.

*Lenticels*.—Approximately 5 per cm.$^2$, slightly raised, approximately 1 mm. long, greyed-orange (RHS 163D) in color.

*New growth bark*.—Grey-brown (RHS 201A) in color.

Leaves:

*Texture*.—Upper surface leathery; lower surface velvety.

*Length*.—10 cm.

*Width*.—Typically between 5 and 6 cm., folding upward.

*Apex*.—Slight cuspidate, medium thick.

*Venation*.—Reticulate pattern.

*Margin*.—Fine, coarsely serrate.

*Petioles*.—Generally, between 2.5 and 3 cm. long, and about 2 mm. in diameter at the mid-section. Color is green (RHS 145C) with some red at base (RHS 53B).

*Stipules*.—0-2, with an average length between 1 and 1.5 cm. Color is green (RHS 137B).

Leaf color:

*Upper leaf surface*.—Dark green (RHS 137A).

*Lower leaf surface*.—Yellow-green (RHS 139B).

*Vein*.—Yellow-green (RHS 145C).

Flowers:

*Size*.—Corolla diameter averaging about 3.8 cm.

*Petals*.—Typically five, intermediate arrangement, soft texture.

*Color*.—Dormant bud is red-purple (RHS 60D), young flower buds are red-purple (RHS 68B), balloons are red-purple (RHS 68D). Open flowers are white (RHS 155D).

*Bloom season*.—Mid-season. Onset of first and full bloom in Adams County, PA in 2016 was April 19, full bloom on April 23.

Fruit:

*Size*.—Large, averaging 10 cm. in diameter, and between 7.9 and 8.5 cm. high.

*Shape*.—Globose.

*Color*.—Medium overcolor intensity, width of stripes is broad, overcolor pattern is solid flush with weakly defined stripes, deep scarlet red (RHS 45C) generally as a blush of 80-90% over the surface, with some sun-exposed areas being Red Group color (RHS 53A). Areas of ground color are Greyed-Orange (RHS 167C); lenticels are prominent and Greyed-Orange (RHS 164C); and the stem-pit is Yellow-Green (RHS 145B). The color characteristics of the 'JHB 619 Cltv' fruit differ from those of the fruit of 'Jored', which have a clear bright red color (RHS 45B) extending over about 70-90% of the fruit surface with small, chimaera stripes (from 1 mm to 2 mm in width), and sharply contrasting, bright green-yellow background color (RHS 150 B/C); and lenticels are prominent but of a different and distinct white color (RHS N155D). The color characteristics of the 'JHB 619 Cltv' fruit also differ from those of the fruit of Jonagold De Coster', which have a sun-exposed side coloring of alternating stripes of Greyed-Red (RHS 179B and RHS 179A) with some blush areas (RHS 179C), and a shaded side of fruit and stem pit coloring of Yellow-Green (RHS 145A), which is the same color as the stem pit; and wherein lenticels are have a different Grey-Brown (RHS 199B) color that are inconspicuous in shaded areas of fruit and moderately conspicuous in sun-exposed areas of fruit.

*Skin*.—Smooth, glossy, medium thickness.

*Stem*.—Color is gold, (RHS 22A), lightly pubescent, length between 2 to 2.5 cm., and 2.5 mm. in diameter, thin.

*Cavity*.—Flaring, depth 1.2 cm., breadth between 2.1-2.6 cm. Gold russet markings (RHS 22A).

*Basin*.—Depth between 1.25 and 1.5 cm.; breadth 3.1 cm.

*Calyx*.—Sepals persistent with erect tips, slightly open, diameter 3.5 mm.

*Calyx tube*.—Cone-shaped.

*Lenticels are prominent and greyed-orange color* (*RHS 164C*).—In contrast, the lenticels of the fruit of 'Jored' are prominent but of a distinct white color (RHS N155D), and the lenticels of the fruit of 'Jonagold De Coster' are a grey-brown color (RHS 199B) and inconspicuous in shaded areas of fruit and moderately conspicuous in sun-exposed areas of fruit.

*Russet*.—Slight, mainly around cavity, gold (RHS 1C).

Fruit properties:

*Flesh color*.—Cream (RHS 158D).

*Juice*.—Above average.

*Firmness*.—Medium firm.

*Texture*.—Crisp.

*Flavor*.—Sweet/tart.

*Aroma*.—Aromatic.

*Eating quality*.—Very good.

*Keeping quality*.—Best before 7 months of storage.

*Eating maturity*.—Mid-season.

*Time of fruit harvest*.—Last week of September in Adams County, PA.

*Storage life*.—Best before 7 months of cold storage.

*Market uses*.—Juice, dessert, baking.

*Core*.—Median position; open, axile.

*Core lines*.—Basil, clasping.

*Carpellary area*.—Visible.

*Depth of calyx tube*.—15 mm.

*Seed cells*.—Generally 2 seeds per cell, open, 5 in number.

*Cell walls*.—Thick, obovate in cross-section; length 1 cm., breadth 0.4 cm.

Seeds:

*Number*.—Usually 10.

*Length*.—0.8 cm.

*Breadth*.—0.4 cm.

*Form*.—Acuminate.

*Color*.—Tan (RHS 200C).

*Plant/fruit disease and pest resistance/susceptibility*.—Susceptible to mildew (*Podosphaera leucotricha*), scab (*Venturia inaequalis*) and fire-blight (*Erwinia amylovora*).

We claim:

1. A new and distinct variety of apple tree named 'JHB 619 Cltv', substantially as illustrated and described herein.

* * * * *